US007678916B2

(12) United States Patent
Kankan et al.

(10) Patent No.: US 7,678,916 B2
(45) Date of Patent: Mar. 16, 2010

(54) PROCESS

(75) Inventors: Rajendra Narayanrao Kankan, Maharashtra (IN); Dharmaraj Ramachandra Rao, Maharashtra (IN); Manjinder Singh Phull, Mumbai (IN); Dilip Ramda Birari, Thane (IN)

(73) Assignee: Cipla Limited, Mumbai (IN)

( * ) Notice: Subject to any disclaimer, the term of this patent is extended or adjusted under 35 U.S.C. 154(b) by 856 days.

(21) Appl. No.: 10/569,439

(22) PCT Filed: Aug. 13, 2004

(86) PCT No.: PCT/GB2004/003519

§ 371 (c)(1),
(2), (4) Date: May 1, 2006

(87) PCT Pub. No.: WO2005/021541

PCT Pub. Date: Mar. 10, 2005

(65) Prior Publication Data

US 2006/0264639 A1     Nov. 23, 2006

(30) Foreign Application Priority Data

Aug. 29, 2003   (GB) .................................. 0320304.9

(51) Int. Cl.
*C07D 417/12*        (2006.01)
(52) U.S. Cl. .................................................. 546/269.7
(58) Field of Classification Search ............... 546/269.7
See application file for complete search history.

(56) References Cited

U.S. PATENT DOCUMENTS

2005/0014798 A1* 1/2005 Turchetta et al. ............ 514/342

FOREIGN PATENT DOCUMENTS

WO         0226737        4/2002

OTHER PUBLICATIONS

Synthesis and Biological Activity of Metabolites of the Antidiabetic, Antihyperglycemic Agent Pioglitazone; J. Med. Chem. 1996, vol. 39, 5053-5063.

* cited by examiner

*Primary Examiner*—Patricia L Morris
(74) *Attorney, Agent, or Firm*—Conley Rose, P.C.; Rodney B. Carroll

(57) ABSTRACT

The present invention relates to processes for the preparation of rosiglitazone, rosiglitazone prepared thereby and pharmaceutical compositions and therapeutic uses thereof, and methods of treatment employing the same.

8 Claims, 4 Drawing Sheets

PROCESS

This application is a 35 USC §371 U.S. National Stage Application of International Application No. PCT/GB2004/003519, filed on Aug. 13, 2004, claiming the priority of Great Britain Patent Application No. 0320304.9, filed Aug. 29, 2003, the entire disclosures of which are incorporated herein by reference in their entireties.

The present invention relates to processes for the preparation of rosiglitazone, rosiglitazone prepared thereby and pharmaceutical compositions and therapeutic uses thereof, and methods of treatment employing the same.

Rosiglitazone maleate, 5-[4-[2-(N-methyl-N-(2-pyridyl)amino)ethoxy]benzyl]thiazolidine-2,4-dione maleate, has the following general structural formula (I)

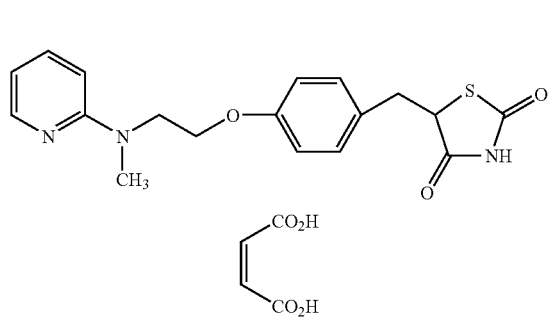

(I)

Rosiglitazone is a member of the thiazolidinedione class of compounds and is one of the most potent compounds of this class. The thiazolidinedione class of antidiabetics, such as pioglitazone, englitazone, rosiglitazone, troglitazone and ciglitazone, has been shown to alleviate insulin resistance in humans. Rosiglitazone is, therefore, a known antidiabetic compound, and more particularly is the preferred drug for non-insulin dependent diabetes mellitus (NIDDM). Diabetes mellitus is a complex, chronically progressive disease, which affects the function of the kidneys, eyes, vascular and nervous systems.

PCT patent application WO 94/05659 discloses certain thiazolidinedione derivatives having hypoglycaemic and hypolipidaemic activity, including 5-[4-[2-(N-methyl-N-2-pyridyl)amino)ethoxy]benzyl]thiazolidine-2,4-dione maleate.

PCT patent applications WO 99/31093, WO 99/31094 and WO 99/31095 disclose distinct hydrates of rosiglitazone maleate having a non-stoichiometric water content.

PCT patent applications WO00/64893, WO00/64896 and WO 02/026737 disclose polymorphs of rosiglitazone maleate. For WO 02/026737, polymorphic forms I, II, III and IV of rosiglitazone maleate are disclosed, processes of preparing the same and pharmaceutical compositions thereof.

The present invention now provides further processes for the preparation of rosiglitazone, including rosiglitazone maleate and also rosiglitazone free base. With respect to the preparation of rosiglitazone maleate according to the present invention, preparation of two polymorphic forms are described, which are hereinafter referred to as Forms A and B. Rosiglitazone maleate Form A is thermodynamically stable, and can be easily made from rosiglitazone maleate Form B, or other anhydrous or hydrated rosiglitazone maleate polymorphs described in the prior art.

Crystalline rosiglitazone maleate Form A as prepared according to the present invention has an X-ray diffraction pattern, or substantially the same X-ray diffraction pattern, as shown in FIG. 1. More particularly, crystalline rosiglitazone maleate Form A can be characterised as having an X-ray diffraction pattern with characteristic peaks (2θ): 9.25°, 15.86°, 15.02°, 17.00°, 18.52°, 21.99°, 23.58°, 25.06° and 26.55°.

Further characterising data for crystalline rosiglitazone maleate Form A as obtained by X-ray diffraction is shown in following table 1.

TABLE 1

| Peak No. | 2θ (deg) | d (A) | I/I1 | FWHM (deg) | Intensity (Counts) | Integrated Intensity (Counts) |
|---|---|---|---|---|---|---|
| 1 | 4.6400 | 19.02888 | 8 | 0.25340 | 110 | 1776 |
| 2 | 7.5303 | 11.73040 | 5 | 0.23400 | 64 | 960 |
| 3 | 8.5239 | 10.36513 | 6 | 0.25440 | 81 | 1507 |
| 4 | 9.2554 | 9.54750 | 10 | 0.25980 | 125 | 1992 |
| 5 | 9.8216 | 8.99833 | 4 | 0.52330 | 48 | 1145 |
| 6 | 13.8862 | 6.37225 | 4 | 0.23250 | 54 | 732 |
| 7 | 15.0298 | 5.88986 | 53 | 0.32920 | 693 | 14134 |
| 8 | 15.8678 | 5.58065 | 100 | 0.29740 | 1296 | 21662 |
| 9 | 17.0012 | 5.21108 | 15 | 0.35970 | 200 | 3772 |
| 10 | 17.7826 | 4.98381 | 4 | 0.23870 | 57 | 826 |
| 11 | 18.5216 | 4.78659 | 31 | 0.36170 | 400 | 7774 |
| 12 | 19.1800 | 4.62374 | 4 | 0.30400 | 50 | 979 |
| 13 | 19.9585 | 4.44511 | 5 | 0.35710 | 61 | 1319 |
| 14 | 21.1312 | 4.20100 | 4 | 0.25750 | 57 | 903 |
| 15 | 21.9976 | 4.03746 | 21 | 0.41060 | 267 | 6470 |
| 16 | 23.5826 | 3.76956 | 15 | 0.36270 | 198 | 4075 |
| 17 | 24.5000 | 3.63045 | 8 | 0.32880 | 99 | 2208 |
| 18 | 25.0693 | 3.54928 | 39 | 0.40300 | 501 | 11039 |
| 19 | 26.1200 | 3.40884 | 5 | 0.25000 | 60 | 878 |
| 20 | 26.5587 | 3.35352 | 11 | 0.48250 | 141 | 3200 |
| 21 | 27.2400 | 3.27117 | 4 | 0.34220 | 48 | 901 |
| 22 | 28.2400 | 3.15757 | 4 | 0.54660 | 58 | 1647 |
| 23 | 30.0716 | 2.96929 | 5 | 0.74330 | 70 | 2483 |
| 24 | 31.1400 | 2.86980 | 4 | 0.24000 | 47 | 587 |
| 25 | 31.4600 | 2.84134 | 3 | 0.39340 | 42 | 753 |
| 26 | 31.9916 | 2.79533 | 4 | 0.44330 | 52 | 1436 |
| 27 | 33.9765 | 2.63643 | 5 | 0.25700 | 69 | 1236 |
| 28 | 34.6694 | 2.58531 | 5 | 0.11530 | 63 | 384 |

Crystalline rosiglitazone maleate Form A can also be characterised as having an infra red absorption spectrum, or substantially the same infra red absorption spectrum, as shown in FIG. 2. Characteristic peaks are as follows: 1750, 1705, 1640, 1619, 1514, 1466, 1379, 1361, 1326, 1242, 1163, 866, 774, 715 and 669 $cm^{-1}$. The infrared spectrum was obtained with a mineral oil dispersion of the rosiglitazone maleate Form A, using a Perkin Elmer spectrum-1 FT IR spectrometer.

Crystalline rosiglitazone maleate Form B as prepared according to the present invention has an X-ray diffraction pattern, or substantially the same X-ray diffraction pattern, as shown in FIG. 3. More particularly, crystalline rosiglitazone maleate Form B can be characterised as having an X-ray diffraction pattern with characteristic peaks (2θ): 8.939°, 15.37°, 15.86°, 18.05°, 20.24°, 22.28°, 23.51°, 24.88°, 25.12°, 25.91°, 26.69° and 29.64°.

Further characterising data for crystalline rosiglitazone maleate Form B as obtained by X-ray diffraction is shown in following table 2.

TABLE 2

| Peak No. | 2θ (deg) | d (A) | I/I1 | FWHM (deg) | Intensity (Counts) | Integrated Intensity (Counts) |
|---|---|---|---|---|---|---|
| 1 | 4.6817 | 18.85948 | 6 | 0.20790 | 112 | 1615 |
| 2 | 8.9294 | 9.89532 | 16 | 0.22310 | 273 | 3878 |

TABLE 2-continued

| Peak No. | 2θ (deg) | d (A) | I/I1 | FWHM (deg) | Intensity (Counts) | Integrated Intensity (Counts) |
|---|---|---|---|---|---|---|
| 3 | 9.3175 | 9.48401 | 3 | 0.27500 | 58 | 806 |
| 4 | 12.0317 | 7.34994 | 4 | 0.25000 | 68 | 1071 |
| 5 | 13.9812 | 6.32916 | 6 | 0.27180 | 101 | 1604 |
| 6 | 14.8200 | 5.97277 | 3 | 0.09000 | 60 | 649 |
| 7 | 15.3798 | 5.75661 | 100 | 0.32560 | 1759 | 29961 |
| 8 | 15.8639 | 5.58201 | 10 | 0.40280 | 182 | 3362 |
| 9 | 16.7804 | 5.27914 | 9 | 0.24520 | 166 | 2342 |
| 10 | 18.0501 | 4.91055 | 19 | 0.27940 | 343 | 5704 |
| 11 | 18.7600 | 4.72630 | 3 | 0.20000 | 54 | 572 |
| 12 | 19.1934 | 4.62054 | 9 | 0.34950 | 158 | 2634 |
| 13 | 19.6600 | 4.51192 | 6 | 0.42000 | 112 | 1883 |
| 14 | 19.9800 | 4.44038 | 9 | 0.20360 | 164 | 1511 |
| 15 | 20.2400 | 4.38392 | 13 | 0.24300 | 230 | 2888 |
| 16 | 20.7539 | 4.27651 | 9 | 0.25870 | 162 | 2226 |
| 17 | 21.1716 | 4.19307 | 4 | 0.24330 | 68 | 834 |
| 18 | 22.2847 | 3.98609 | 23 | 0.31550 | 404 | 7057 |
| 19 | 23.1200 | 3.84393 | 4 | 0.10000 | 72 | 498 |
| 20 | 23.5140 | 3.78040 | 17 | 0.43750 | 294 | 5969 |
| 21 | 24.0600 | 3.69583 | 4 | 0.38280 | 69 | 1193 |
| 22 | 24.2800 | 3.66284 | 6 | 0.19400 | 110 | 901 |
| 23 | 24.8800 | 3.57585 | 16 | 0.37000 | 283 | 5014 |
| 24 | 25.1200 | 3.54223 | 23 | 0.18920 | 399 | 3534 |
| 25 | 25.4200 | 3.50110 | 4 | 0.22400 | 71 | 1065 |
| 26 | 25.9188 | 3.43484 | 11 | 0.42770 | 195 | 3233 |
| 27 | 26.1800 | 3.40116 | 4 | 0.23360 | 63 | 868 |
| 28 | 26.6929 | 3.33696 | 11 | 0.29410 | 193 | 2721 |
| 29 | 27.1084 | 3.28675 | 6 | 0.30690 | 112 | 1674 |
| 30 | 28.1400 | 3.16856 | 6 | 0.26660 | 110 | 1517 |
| 31 | 28.4000 | 3.14014 | 4 | 0.15280 | 69 | 633 |
| 32 | 28.7375 | 3.10403 | 4 | 0.23500 | 76 | 887 |
| 33 | 29.2800 | 3.04774 | 8 | 0.41000 | 149 | 5056 |
| 34 | 29.6400 | 3.01153 | 15 | 0.00000 | 256 | 0 |
| 35 | 29.8000 | 2.99573 | 9 | 0.25240 | 159 | 2457 |
| 36 | 30.2125 | 2.95576 | 3 | 0.35500 | 54 | 1367 |
| 37 | 31.5203 | 2.83604 | 4 | 0.43060 | 69 | 2168 |
| 38 | 33.1837 | 2.69758 | 9 | 0.36170 | 152 | 3225 |
| 39 | 35.6175 | 2.51863 | 3 | 0.28160 | 53 | 1541 |
| 40 | 38.6400 | 2.32829 | 3 | 0.41340 | 58 | 1132 |
| 41 | 38.8200 | 2.31791 | 4 | 0.45600 | 66 | 1023 |

Crystalline rosiglitazone maleate Form B can also be characterised as having an infra red absorption spectrum, or substantially the same infra red absorption spectrum, as shown in FIG. 4. Characteristic peaks are as follows: 1745, 1708, 1641, 1619, 1464, 1484, 1378, 1354, 1303, 1245, 1179, 1164, 1084, 1071, 862, 824, 778 and 719 cm$^{-1}$. The infrared spectrum was obtained with a mineral oil dispersion of the rosiglitazone maleate Form B, using a Perkin Elmer spectrum-1 FT IR spectrometer.

There is now provided by the present invention a process of preparing crystalline rosiglitazone maleate Form A, characterised as having an X-ray diffraction pattern with characteristic peaks (2θ): 9.5, 15.86, 15.02, 17.00, 18.52, 21.99, 23.58, 25.06 and 26.55, which process comprises preparing a mixture which comprises rosiglitazone free base, and maleic acid, present in a water miscible solvent, stirring said mixture and heating to obtain a solution, filtering to obtain a clear filtrate and adding a water immiscible solvent thereto, followed by stirring and cooling so as to isolate crystalline rosiglitazone maleate Form A.

Suitably a water miscible solvent employed in the above process is a $C_{1-4}$alcohol, with the use of methanol being preferred.

Preferably the initial mixture obtained in the above process is heated to a temperature of at least about 45° C. to obtain the solution, suitably to a temperature in the range of about 45-50° C.

Preferably the water immiscible solvent is ethyl acetate, which is suitably added to the filtrate with stirring at a temperature in the range of about 25-30° C., followed by further stirring suitably for about 1 hour whilst maintaining the temperature at about 30° C.

Typically cooling is to a temperature in the range of about 5-10° C., with further stirring, suitably for about 1 hour, whilst essentially maintaining the temperature as above. Resulting solid is filtered, washed with ethyl acetate, and dried under vacuum to obtain rosiglitazone maleate Form A.

There is also provided by the present invention a process of preparing crystalline rosiglitazone maleate Form A, characterised as having an X-ray diffraction pattern with characteristic peaks (2θ): 9.5, 15.86, 15.02, 17.00, 18.52, 21.99, 23.58, 25.06 and 26.55, which process comprises preparing a mixture which comprises rosiglitazone free base, and maleic acid, present in a solvent therefor, refluxing said mixture, filtering said mixture and obtaining a filtrate, adding seed crystals of rosiglitazone maleate Form A to said filtrate, followed by stirring and isolating crystalline rosiglitazone maleate Form A.

Suitably the solvent employed is acetone and the seed crystals of rosiglitazone maleate Form A are added at a temperature in the range of about 35-40° C., typically about 40° C., followed by stirring at a reduced temperature (typically at about 30° C.) for an extended period of time which is usually about 18 hours.

The process suitably further comprises drying under vacuum initially at a temperature in the range of about 25-35° C., typically at about 30° C. and for about 5 hours, and subsequently at a temperature in the range of about 45-55° C., typically about 50° C. and for about 6 hours, to obtain rosiglitazone maleate Form A.

There is further provided by the present invention a process of preparing crystalline rosiglitazone maleate Form A, characterised as having an X-ray diffraction pattern with characteristic peaks (2θ): 9.5, 15.86, 15.02, 17.00, 18.52, 21.99, 23.58, 25.06 and 26.55, which process comprises preparing a mixture which comprises rosiglitazone free base, and maleic acid, present in a solvent therefor, refluxing said mixture, cooling said mixture and stirring so as to obtain precipitated solid, filtering said precipitated solid and drying to yield crystalline rosiglitazone maleate Form A.

Suitably the solvent is acetonitrile and cooling is typically to a temperature in the range of about 25-35° C., suitably about 30° C., followed by stirring suitably for about 5 hours at a temperature in the range of 25-30° C. to obtain the precipitated solid.

The process suitably further comprises drying under vacuum at a temperature in the range of about 25-35° C., typically at about 30° C. for about 5 hours, and subsequently at a temperature in the range of about 45-55° C., typically at about 50° C. for about 6 hours, to obtain rosiglitazone maleate Form A.

There is also provided by the present invention a process of preparing crystalline rosiglitazone maleate Form A, characterised as having an X-ray diffraction pattern with characteristic peaks (2θ): 9.5, 15.86, 15.02, 17.00, 18.52, 21.99, 23.58, 25.06 and 26.55, which process comprises suspending a rosiglitazone maleate polymorph, or a hydrate of rosiglitazone maleate, in a solvent and heating to obtain a solution, cooling and stirring said solution, and isolating crystalline rosiglitazone maleate Form A.

Preferably the solvent is a $C_{1-4}$alcohol, such as isopropyl alcohol, and the solution is obtained by heating to a temperature in the range of about 60-65° C. The solution is suitably cooled to a temperature in the range of about 25-30° C. and stirred for an extended period of time, such as about 8 hours. Crystals obtained further to the cooling are filtered and dried under vacuum at a temperature in the range of about 45-55° C., about 50° C., to obtain rosiglitazone maleate Form A.

Alternatively it may be preferred that the solvent is ethyl acetate and wherein the solution is obtained by heating to a temperature in the range of about 60-65° C. Cooling is then to a temperature of about 20-25° C., with stirring, followed by further cooling to a temperature of less than about 10° C., typically about 5° C. Resulting solid is filtered, washed with ethyl acetate and dried under vacuum at a temperature in the range of about 45-55° C., about 50° C., to obtain rosiglitazone maleate Form A.

There is also provided by the present invention a process of preparing crystalline rosiglitazone maleate Form B, characterised as having an X-ray diffraction pattern with characteristic peaks (2θ): 8.93, 15.37, 15.86, 18.05, 20.24, 22.28, 23.51, 24.88, 25.12, 25.91, 26.69 and 29.64, which process comprises suspending rosiglitazone maleate Form A, characterised as having an X-ray diffraction pattern with characteristic peaks (2θ): 9.5, 15.86, 15.02, 17.00, 18.52, 21.99, 23.58, 25.06 and 26.55, in a solvent and heating to obtain a solution, cooling and leaving to stand, and isolating crystalline rosiglitazone maleate Form B.

Preferably the solvent is a $C_{1-4}$ alcohol, such as isopropyl alcohol, and the solution is suitably obtained by heating to a temperature in the range of about 60-65° C. Alternatively, the solvent can be tetrahydrofuran, with the solution being obtained by heating to reflux.

The resulting solution is kept standing at a temperature in the range of about 0 to −5° C. for an extended period of time, at least about 48 hours, and the resulting crystals filtered and dried under vacuum at a temperature in the range of about 45-55° C., suitably about 50° C., to obtain rosiglitazone maleate Form B.

The present invention also provides a process of preparing rosiglitazone free base by reduction of 5-[4-[2-(N-methyl-N-(2-pyridyl)amino)ethoxy]benzylidene]thiazolidine-2,4-dione of formula (II)

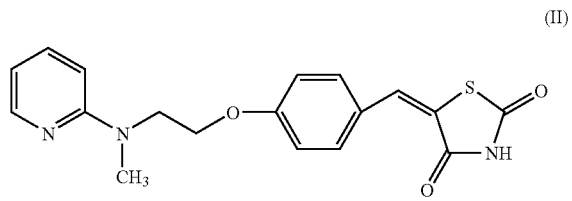

(II)

in the presence of a cobalt ion, a ligand and a reducing agent, wherein:

the cobalt ion is provided in the form of any of the following—cobaltous chloride, cobaltous diacetate and cobaltic chloride;

the ligand is selected from the group consisting of dimethylglyoxime, 2,2'-bipyridyl and 1,10-phenanthroline;

the reducing agent is selected from the group consisting of sodium borohydride, lithium borohydride, potassium borohydride, tetraalkylammonium borohydride and zinc borohydride;

and optionally converting the thus formed rosiglitazone free base to a pharmaceutically acceptable salt thereof.

Preferably the above process is carried out in the presence of cobaltous chloride as the source of the cobalt ion, and/or dimethylglyoxime as the ligand and/or sodium borohydride as the reducing agent. A compound of formula (II) can be readily be prepared by synthetic techniques well known in the art, for example as referred to in U.S. Pat. No. 5,585,495.

It is further preferred that 5-[4-[2-(N-methyl-N-(2-pyridyl) amino)ethoxy]benzylidene]thiazolidine-2,4-dione of formula (II) is suspended in tetrahydrofuran in the presence of a base, where the base is an alkali metal hydroxide, such as sodium hydroxide. Suitably, a reaction mixture comprising 5-[4-[2-(N-methyl-N-2-pyridyl)amino)ethoxy]benzylidene] thiazolidine-2,4-dione, cobaltous chloride, dimethylglyoxime and sodium borohydride in the presence of tetrahydrofuran as a solvent is stirred for an extended period of time, typically about 16 hours, at a temperature in the range of about 20-30° C.

Further to the above stirring, the reaction mixture is suitably acidified, for example by the addition of glacial acetic acid over a period of about 1 to 2 hours. Preferably, the resulting suspension is further stirred for a period of about 1 to 2 hours, the solid obtained filtered, washed with water and dried under vacuum at a temperature of about 55-65° C., typically about 60° C., to obtain rosiglitazone free base.

Suitable pharmaceutically acceptable acids of rosiglitazone as provided by a process according to the present invention include salts formed with mineral acids, such as hydrobromic, hydrochloric, and sulphuric acids, or organic acids, such as methanesulphonic, tartaric and maleic acids. In particular, it can be preferred that rosiglitazone free base as prepared by a process according to the present invention is converted to rosiglitazone maleate, and in particular rosiglitazone maleate Form A, or Form B, employing process steps for the preparation of these polymorphic forms substantially as hereinbefore described.

The present invention further provides rosiglitazone free base, rosiglitazone maleate Form A or rosiglitazone maleate Form B, substantially as prepared by a process as hereinbefore described.

Rosiglitazone as prepared by the present invention is useful in the treatment of Type II diabetes mellitus. Rosiglitazone as prepared by the present invention can also be indicated to be of particular use for the treatment and/or prophylaxis of other diseases including hyperlipidaemia, hypertension and cardiovascular disease, especially atherosclerosis. In addition, rosiglitazone as prepared by the present invention is considered to be useful for treating certain eating disorders, in particular the regulation of appetite and food intake in subjects suffering from disorders associated with under-eating, such as anorexia nervous, and disorders associated with over-eating, such as obesity and anorexia bulimia.

The present invention accordingly provides, therefore, for use in therapy rosiglitazone as prepared by the present invention.

Accordingly, the present invention provides for use in the treatment of and/or prophylaxis of hyperglycaemia, rosiglitazone as prepared by the present invention. In particular, there is provided rosiglitazone as prepared by the present invention, for use in the treatment of diabetes mellitus.

The present invention further provides for use in the treatment and/or prophylaxis of hyperlipidaemia, rosiglitazone as prepared by the present invention.

The present invention also further provides for use in the treatment of hypertension, cardiovascular disease and certain eating disorders, rosiglitazone as prepared by the present invention. Cardiovascular disease includes in particular atherosclerosis. Certain eating disorders include in particular the regulation of appetite and food intake in, subjects suffering from disorders associated with under-eating, such as anorexia nervosa and disorders associated with over-eating, such as obesity and anorexia bulimia.

Accordingly, the present invention also provides a pharmaceutical composition comprising rosiglitazone as prepared by the present invention, and a pharmaceutically acceptable carrier therefor. In particular, rosiglitazone maleate Form A as prepared by the present invention is suitable for use in pharmaceutical compositions, as it is anhydrous, a free flowing crystal and non-hygroscopic. Preferably a composition as provided by the present invention can be for oral administration. The pharmaceutical compositions of the invention may, however, be administered in any suitable way and in any suitable form, for example orally in the form of tablets, capsules, liquid preparations, granules, lozenges, or parenterally in the form of injectable, or infusible, solutions or suspensions.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents can comprise: corn starch, potato starch, talcum, magnesium stearate, gelatine, lactose, gums, and the like. Any other adjuvant or additive colourings, aroma, preservatives or the like may also be used provided that they are compatible with the rosiglitazone as provided by the present invention.

Solutions for injections may be prepared by dissolving rosiglitazone as provided by the present invention and possible additives in a part of the solvent for injection, typically sterile water, adjusting the solution to the desired volume, sterilisation of the solution and filling in suitable ampoules or vials. Any suitable additive conventionally used in the art may be added, such as tonicity agents, preservatives, antioxidants and the like.

The, present invention further provides a method for the treatment and/or prophylaxis of hyperglycaemia in a patient, which method comprises administering a therapeutically effective amount of rosiglitazone as prepared by the present invention, to a hyperglycaemic patient in need thereof. In particular, the present invention provides a method for the treatment and/or prophylaxis of diabetes mellitus in a patient, which method comprises administering a therapeutically effective amount of rosiglitazone as prepared by the present invention, to a patient suffering from, or susceptible to, diabetes mellitus.

The present invention further provides a method for the treatment of hyperlipidaemia in a patient, which comprises administering a therapeutically effective amount of rosiglitazone as prepared by the present invention, to a hyperlipidaemic patient in need thereof.

The present invention further provides a method for the treatment of hypertension, cardiovascular disease or certain eating disorders substantially as hereinbefore described, which comprises administering a therapeutically effective amount of rosiglitazone as prepared by the present invention, to a patient in need thereof.

In a further aspect the present invention provides the use of rosiglitazone as prepared by the present invention, for the manufacture of a medicament for the treatment and/or prophylaxis of hyperglycaemia. In particular, the present invention provides use of rosiglitazone as prepared by the present invention, for the manufacture of a medicament for the treatment and/or prophylaxis of diabetes mellitus.

The present invention also provides the use of rosiglitazone as prepared by the present invention, for the manufacture of a medicament for the treatment and/or prophylaxis of hyperlipidaemia.

The present invention also provides the use of rosiglitazone as prepared by the present invention, for the manufacture of a medicament for the treatment and/or prophylaxis of hypertension, cardiovascular disease or certain eating disorders.

The particular dosage form of rosiglitazone as prepared by the present invention, required for therapeutic use or treatment in accordance with the present invention will depend on the particular disease state being treated, and the symptoms and severity thereof. Dosage, routes of administration, and frequency of dosing are best decided by an attending physician.

The present invention will now be further illustrated by the following Figures and Examples, which do not limit the scope of the invention in any way.

EXAMPLES

Prior Art Preparation 1

Figure 1:
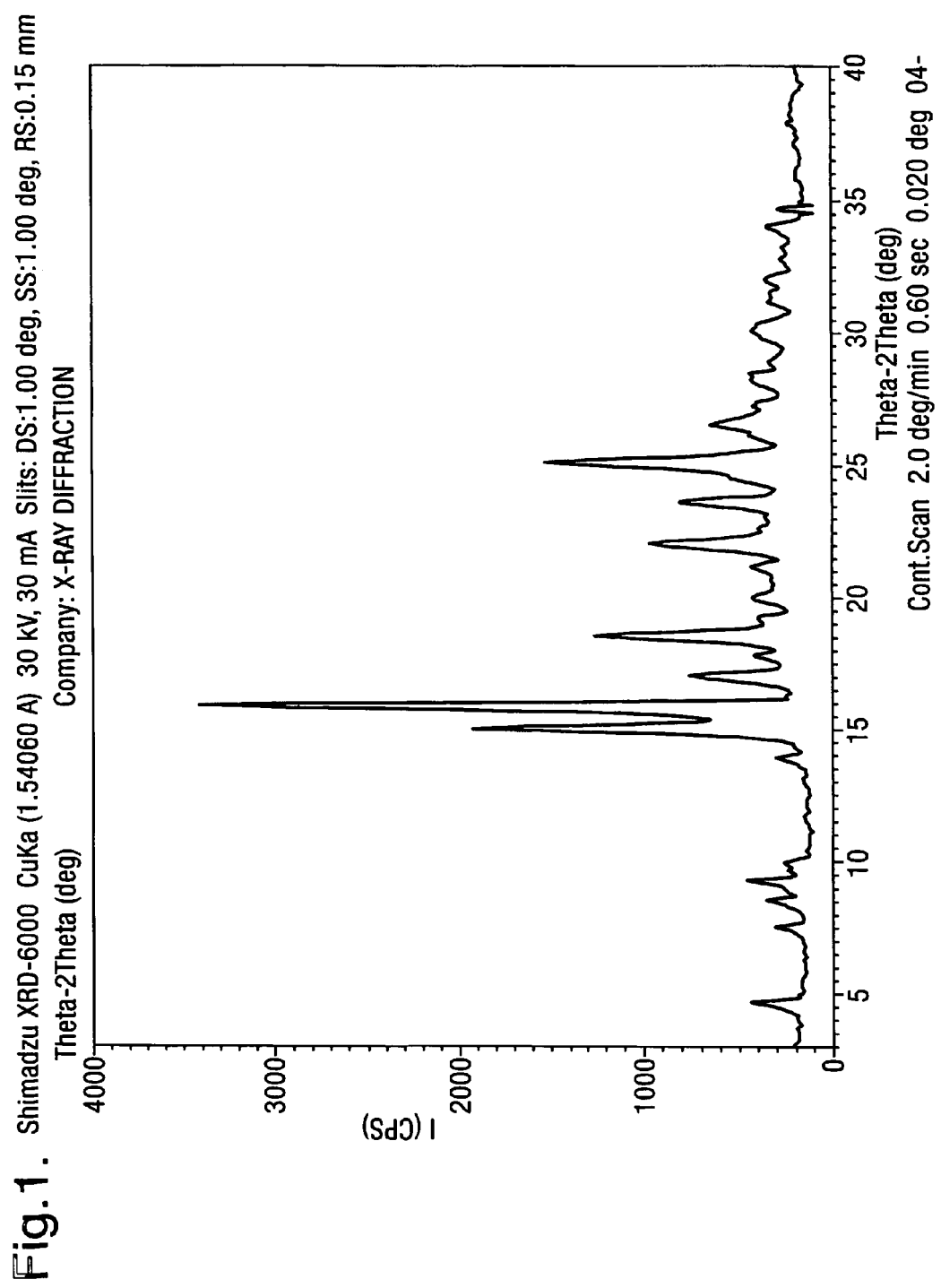
FIG. 1 shows a typical powder XRD pattern of rosiglitazone maleate Form A.
Figure 2:
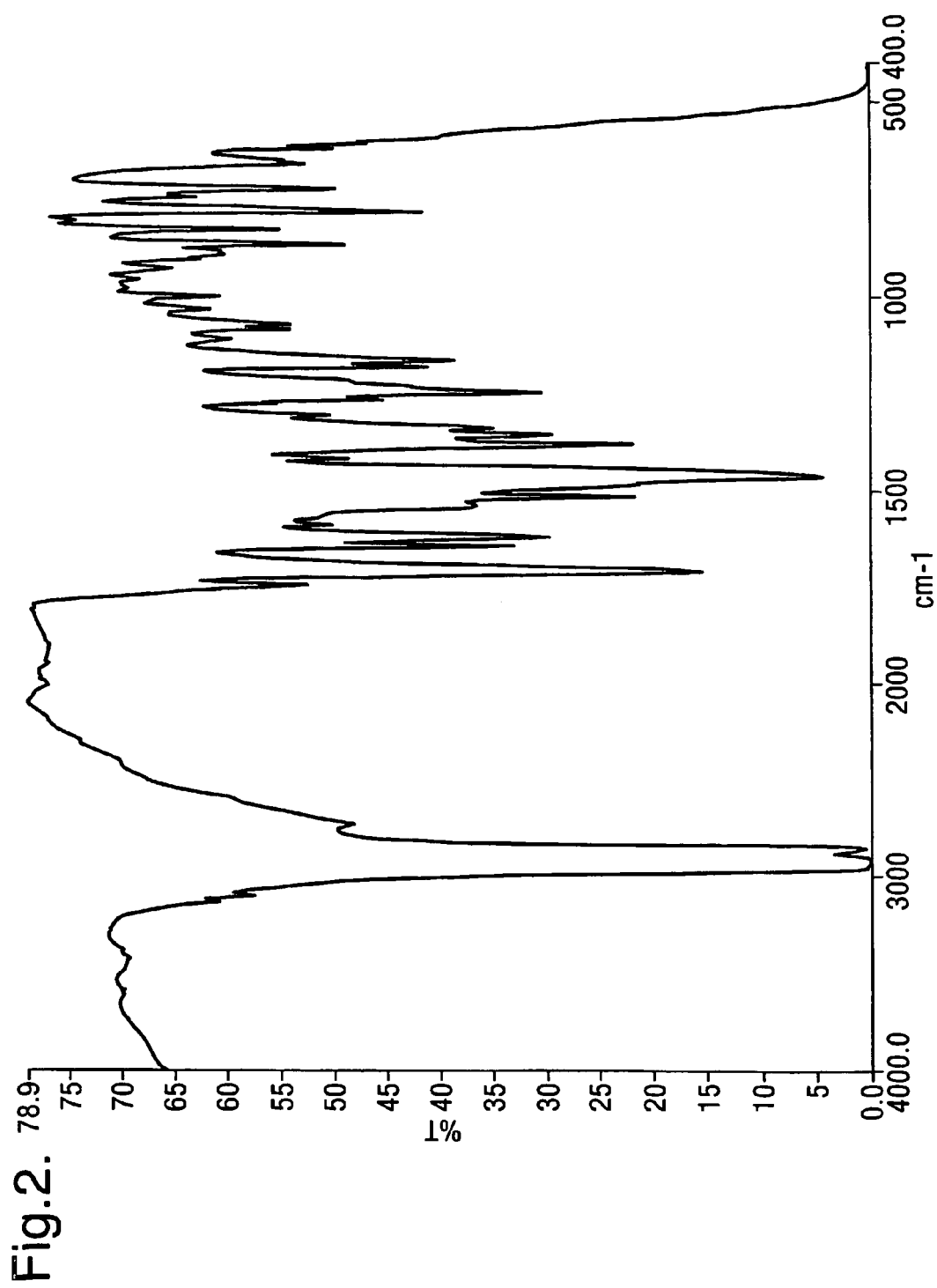
FIG. 2 shows an IR pattern of rosiglitazone maleate Form A.
Figure 3:
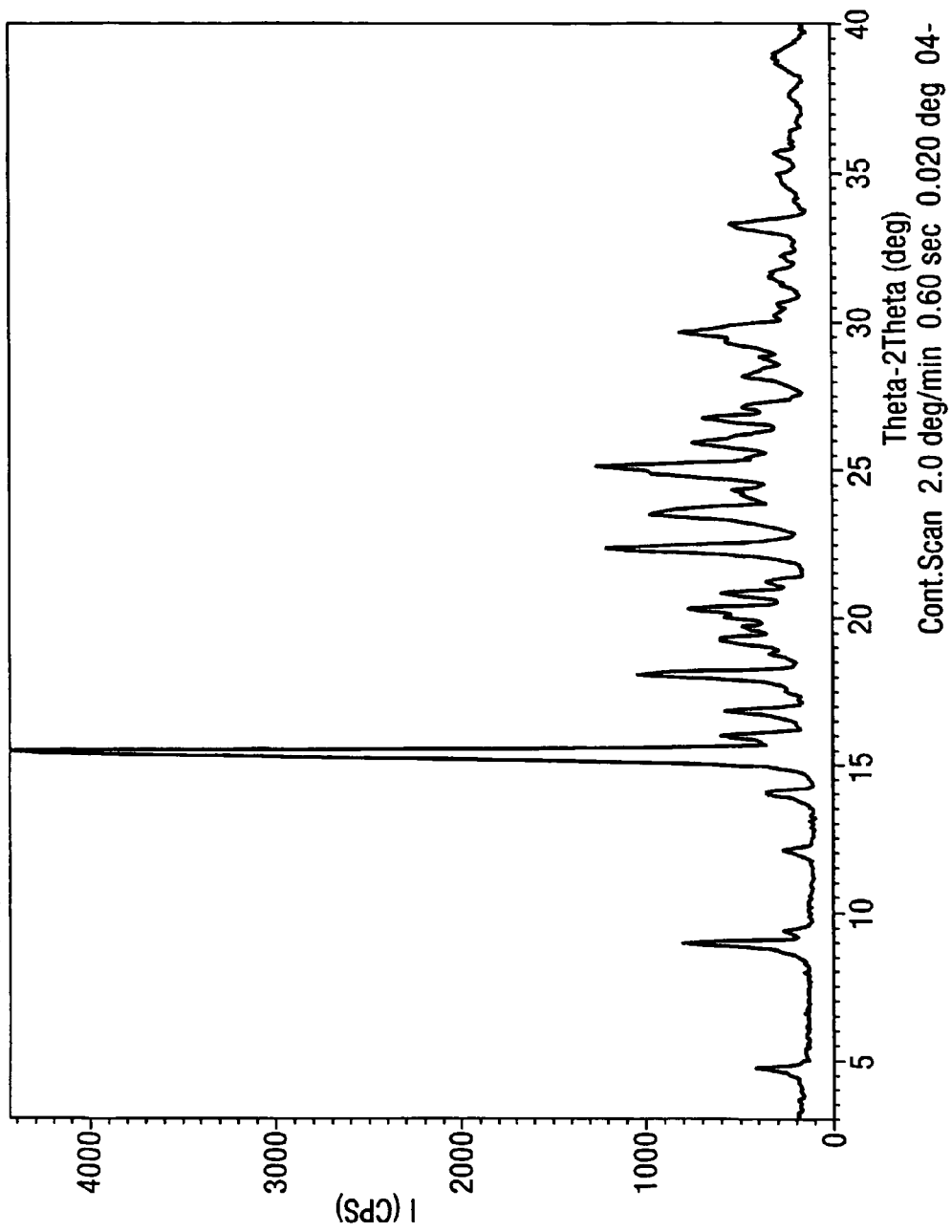
FIG. 3 shows a typical powder XRD pattern of rosiglitazone maleate Form B.
Figure 4:
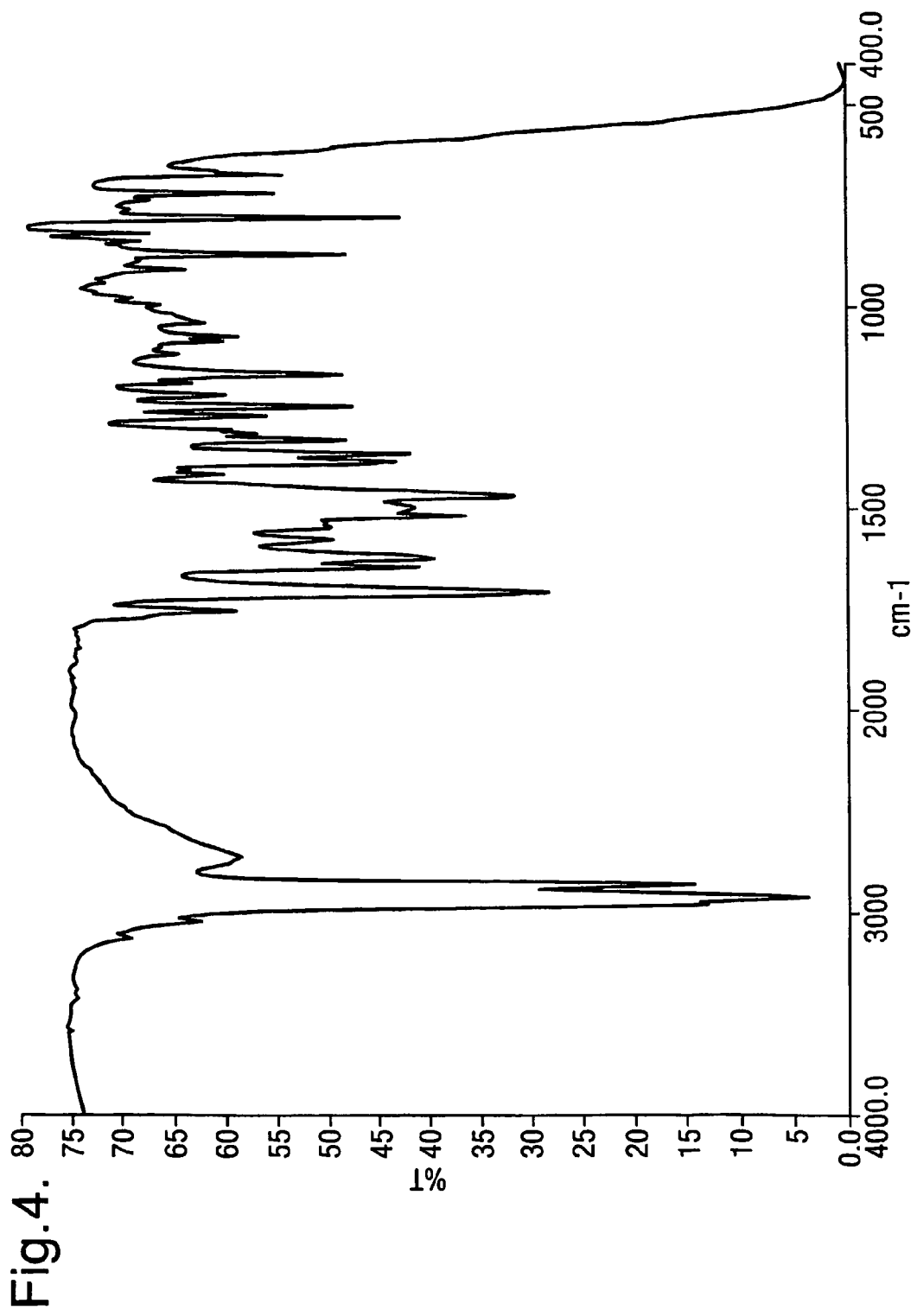
FIG. 4 shows an IR pattern of rosiglitazone maleate Form B.

Rosiglitazone maleate was prepared according to the disclosure of WO 94/05659, in which 5-[4-[2-(N-methyl-N-(2-pyridyl)amino)ethoxy]benzyl]thiazolidine-2,4-dione (470 gms) and maleic acid (137 gms) were dissolved in ethanol (4 ltrs) at boiling. The hot solution was filtered via diatomaceous earth and was then allowed to cool slowly with gentle agitation. After leaving in a refrigerator at 0-5° C. for several hours, the maleate salt was filtered off, washed with ethanol and dried in vacuum at 50° C. to give 446 gms of rosiglitazone maleate as provided by WO 94/05659. The product was characterized as Form-B by XRD & IR, as can be seen by reference to FIGS. 3 and 4 respectively.

Example 1

5-[4-[2-(N-methyl-N-(2-pyridyl)amino)ethoxy]benzylidene]thiazolidine-2,4-dione (10 gms) was suspended in water (30 ml) and tetrahydrofuran (30 ml), and to this suspension was added 25 ml of 4% sodium hydroxide. The resulting mixture was cooled to 10° C. and to this was added a catalyst solution prepared by dissolving 1.88 gms of dimethyl glyoxime and 0.200 gms of cobaltous chloride in 30 ml of tetrahydrofuran. Then a solution of 3.2 gms sodium borohydride, in 30 ml of water, and 9.4 ml of 4% sodium hydroxide, was slowly added at 10° C. over a period of 90 minutes. The resulting reaction mixture was stirred at 25° C. for 16 hours and later was acidified with 60% glacial acetic acid, which was added very slowly over a period of 1 to 2 hours. The resulting suspension was further stirred for 1.5 hours. The solid obtained was filtered and washed with water and dried under vacuum at 60° C. to get 9.3 gms of 5-[4-[2-(N- methyl-N-2-pyridyl)amino)ethoxy]benzyl]thiazolidine-2,4-dione (rosiglitazone free base).

Example 2

5-[4-[2-(N-methyl-N-(2-pyridyl)amino)ethoxy]benzyl]thiazolidine-2,4-dione (rosiglitazone free base, 50 gms, 0.140 mol) was charged in 100 ml methanol and a solution of maleic acid (18.7 gms, 0.16 mol) in methanol (50 ml) was added under stirring and was further heated to 45-50° C. to obtain a clear solution. This solution was filtered (hot) through celite and ethyl acetate (500 ml) was added slowly to this clear filtrate under stirring at 25-30° C., and further stirred for 1 hour at 30° C., then chilled to 5-10° C. and stirred at the same temperature for 1 hour. The solid obtained was filtered under argon atmosphere and washed with 50 ml ethyl acetate. This solid was dried under vacuum at 50-55° C. to get rosiglitazone maleate Form A (60 gms) in 90% yield.

Example 3

5-[4-[2-(N-methyl-N-2-pyridyl)amino)ethoxy]benzyl]thiazolidine-2,4-dione (rosiglitazone free base, 100 gms, 0.280 mol) was suspended in 500 ml of dry acetone and a solution of maleic acid (38.99 gms, 0.336 mol) in 200 ml of dry acetone was added at 27° C. to obtain a clear solution. Activated charcoal (5 gms) was added and refluxed for 30 minutes. The solution was filtered (hot) through celite. To the clear filtrate seeds of Form A were added at 40° C. and stirred for 18 hours at 30° C. The precipitated solid was filtered under argon atmosphere and washed with 100 ml of dry acetone. The resulting solid was dried under vacuum at 30° C. for 5 hours, and at 50° C. for 6 hours, to obtain rosiglitazone maleate Form A (95 gms) in 72% yield.

Example 4

5-[4-[2-(N-methyl-N-(2-pyridyl)amino)ethoxy]benzyl]thiazolidine-2,4-dione (rosiglitazone free base, 50 gms, 0.140 mol) was stirred with 250 ml of dry acetonitrile and a suspension of maleic acid (19.50 gms, 0.168 mol) in 100 ml of dry acetonitrile was added at 27° C. to obtain a clear solution, followed by reflux for 30 minutes at 80-82° C. The reaction mass was gradually allowed to cool to 30° C. and stirred for 5 hours at 25-30° C. The precipitated solid was filtered under argon atmosphere and washed with 50 ml of dry acetonitrile. The filtered solid obtained was dried under vacuum at 30° C. for 5 hours, and at 50° C. for 6 hours, to obtain rosiglitazone maleate Form A (45 gms) in 71% yield.

Example 5

Rosiglitazone maleate Form B (50 gms, 0.105 mol) was suspended in 1500 ml of isopropyl alcohol and heated to 60-65° C. to obtain a clear solution. The solution was gradually cooled to 27° C. and stirred for 8 hours. The crystals obtained were filtered and dried under vacuum at 50° C. to obtain rosiglitazone maleate Form A (40 gms) in 80% yield.

Example 6

5-[4-[2-(N-methyl-N-(2-pyridyl)amino)ethoxy]benzyl]thiazolidine-2,4-dione (rosiglitazone free base, 25 gms, 0.07 mol) was suspended in 900 ml of acetone, to which a solution of maleic acid (9.74 gms, 0.083 mol) in 25 ml of methanol was added dropwise for 20 minutes at 25° C. To the above obtained clear solution activated charcoal (5.0 gms) was added and stirred at 25° C. for 20 minutes and subsequently filtered through celite. The resulting clear filtrate was stirred for 12 hours at ambient temperature. The precipitated solid was isolated by filtration and dried under vacuum at 50° C., which gave the desired rosiglitazone maleate Form B (20 gms).

Example 7

Rosiglitazone maleate Form A (20 gms, 0.105 mol) was suspended in 600 ml of isopropyl alcohol and heated to 60-65° C. to obtain a clear solution. The solution was kept standing at 0 to −5° C. for 48 hours. The crystals obtained were filtered and dried under vacuum at 50° C. to obtain rosiglitazone maleate Form B (15.0 gms).

Example 8

Rosiglitazone maleate Form A (20 gms, 0.105 mol) was suspended in 400 ml of tetrahydrofuran and heated to reflux to obtain a clear solution. The solution was kept standing at 0 to −5° C. for several days. The crystals obtained were filtered and dried under vacuum at 50° C. to obtain rosiglitazone maleate Form B (16.0 gms).

Example 9

Rosiglitazone maleate Form B (50 gms) was suspended in 500 ml ethyl acetate and heated to 60° C. in an inert atmosphere, the resulting solution was cooled rapidly under stirring to 25° C., then cooled to 5° C. The solid obtained was filtered, washed with chilled ethyl acetate and dried under vacuum at 50° C., to obtain rosiglitazone maleate Form A.

The invention claimed is:

1. A process of preparing crystalline rosiglitazone maleate Form A, having an X-ray diffraction pattern with characteristic peaks (2θ): 9.5, 15.86, 15.02, 17.00, 18.52, 21.99, 23.58, 25.06 and 26.55, which process comprises preparing a mixture which comprises rosiglitazone free base, and maleic acid, present in a water miscible solvent, stirring said mixture and heating to obtain a solution, filtering the solution to obtain a clear filtrate and adding a water immiscible solvent thereto, followed by stirring and cooling so as to isolate crystalline rosiglitazone maleate Form A.

2. A process according to claim 1, wherein said water miscible solvent is a $C_{1-4}$ alcohol.

3. A process according to claim 2, wherein said $C_{1-4}$ alcohol is methanol.

4. A process according to claim 1, wherein said mixture is heated to a temperature of at least about 45° C. to obtain said solution.

5. A process according to claim 1, wherein said water immiscible solvent is ethyl acetate.

6. A process according to claim 5, wherein said ethyl acetate is added to said filtrate with stirring at a temperature in the range of about 25-30° C., followed by further stirring.

7. A process according to claim 1, wherein said cooling is to a temperature in the range of about 5-10° C., with further stirring whilst essentially maintaining the temperature as above.

8. A process according to claim 7, wherein solid obtained further to said cooling is filtered, washed with ethyl acetate, and dried under vacuum to obtain rosiglitazone maleate Form A.

* * * * *

UNITED STATES PATENT AND TRADEMARK OFFICE
CERTIFICATE OF CORRECTION

PATENT NO. : 7,678,916 B2  Page 1 of 1
APPLICATION NO. : 10/569439
DATED : March 16, 2010
INVENTOR(S) : Rajendra Narayanrao Kankan et al.

It is certified that error appears in the above-identified patent and that said Letters Patent is hereby corrected as shown below:

On Title page of patent, Section (75) Inventors, please correct the name of the fourth inventor from "Dilip Ramda Birari" to -- Dilip Ramdas Birari --

Signed and Sealed this

Eleventh Day of May, 2010

David J. Kappos
*Director of the United States Patent and Trademark Office*